US007413855B2

(12) United States Patent
Bergmann et al.

(10) Patent No.: US 7,413,855 B2
(45) Date of Patent: Aug. 19, 2008

(54) METHOD FOR BISULFITE TREATMENT

(75) Inventors: Frank Bergmann, Iffeldorf (DE);
Christine Markert-Hahn, Penzberg (DE); Joerg Kleibler, Penzberg (DE); Dirk Block, Bichl (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 10/540,406

(22) PCT Filed: Jan. 28, 2004

(86) PCT No.: PCT/EP2004/000729

§ 371 (c)(1),
(2), (4) Date: Jun. 24, 2005

(87) PCT Pub. No.: WO2004/067545

PCT Pub. Date: Aug. 12, 2004

(65) Prior Publication Data

US 2006/0058518 A1    Mar. 16, 2006

(30) Foreign Application Priority Data

Jan. 29, 2003  (EP) ................................. 03001854
May 2, 2003   (EP) ................................. 03010020

(51) Int. Cl.
*C12Q 1/68*    (2006.01)
*C12P 19/34*   (2006.01)
(52) U.S. Cl. ......................................... 435/6; 435/91.4
(58) Field of Classification Search ....................... None
See application file for complete search history.

(56) References Cited

U.S. PATENT DOCUMENTS

| 4,683,202 | A | 7/1987 | Mullis et al. ................. 435/91 |
| 5,130,238 | A | 7/1992 | Malek et al. ................. 435/91 |
| 5,137,806 | A | 8/1992 | LeMaistre et al. ............... 435/6 |
| 5,210,015 | A | 5/1993 | Gelfand et al. ................ 435/6 |
| 5,234,809 | A | 8/1993 | Boom et al. ................. 435/91 |
| 5,487,972 | A | 1/1996 | Gelfand et al. ................ 435/6 |
| 5,552,277 | A | 9/1996 | Nelson et al. ................. 435/6 |
| 5,595,890 | A | 1/1997 | Newton et al. ............. 435/91.2 |
| 5,639,611 | A | 6/1997 | Wallace et al. ................ 435/6 |
| 5,786,146 | A | 7/1998 | Herman et al. ................ 435/6 |
| 5,804,375 | A | 9/1998 | Gelfand et al. ................ 435/6 |
| 6,174,670 | B1 | 1/2001 | Wittwer et al. ................ 435/6 |
| 6,331,393 | B1 | 12/2001 | Laird et al. ................... 435/6 |

FOREIGN PATENT DOCUMENTS

| EP | 0 200 362 B1 | 12/1986 |
| EP | 0 201 184 B1 | 12/1986 |
| EP | 0 389 063 B1 | 9/1990 |
| EP | 0 439 182 B1 | 7/1991 |
| EP | 1 394 172 A1 | 3/2004 |
| WO | WO 90/01069 | 2/1990 |
| WO | WO 92/008800 | 1/1992 |
| WO | WO 92/02638 | 2/1992 |
| WO | WO 96/41811 | 12/1996 |
| WO | WO 99/16781 | 4/1999 |
| WO | WO 99/40098 | 8/1999 |
| WO | WO 00/32762 | 6/2000 |
| WO | WO 00/37291 | 6/2000 |
| WO | WO 01/37291 A1 | 5/2001 |
| WO | WO 01/98528 A2 | 12/2001 |
| WO | WO 02/31186 A2 | 4/2002 |

OTHER PUBLICATIONS

Abramson, R., et al., 1993, "Nucleic acid amplification technologies", *Current Opinion in Biotechnology*, 4:41-47.
Alderton, R., et al., 1992, "Magnetic Bead Purification of M13 DNA Sequencing Templates", *Analytical Biochemistry*, 201:166-169.
Ausubel F., et al., 2001, "Current Protocols In Molecular Biology", *John Wiley & Sons, Inc.*, Supplement 55-56:1-10.
Barany, F., 1991, "The Ligase chain Reaction in a PCR World", *PCR Methods and Applications*, 5-16.
Barany, F., 1991, "Genetic disease detection and DNA amplification using cloned thermostable ligase", *Proc. Natl. Acad. Sci. USA*, 88:189-193.
Benyajati, C., et al., "Alcohol dehydrogenase in Drosophila: isolation and characterization of messenger RNA and cDNA clone", *Nucleic Acids Research*, 8:5649-5667.
Clark, S., et al., 1994, "High sensitivity mapping of methylated cytosines", *Nucleic Acids Research*, 22(15):2990-2997.
Feil, R., et al., 1994, "Methylation analysis on individual chromosomes: improved protocol for bisulphate genomic sequencing", *Oxford University Press*, 22(4):695-696.
Frommer, M., 1992, "A genomic sequencing protocol that yields a positive display of 5-methylcytosine risidues in individual DNA strands", *Proc. Natl. Sci. USA*, 89:1827-1831.

(Continued)

*Primary Examiner*—Kenneth R. Horlick
*Assistant Examiner*—David C Thomas
(74) *Attorney, Agent, or Firm*—Olga Kay; Charles M. Doyle

(57) ABSTRACT

The present application is directed to a method for performing a bisulfite reaction to determine methylation positions in a nucleic acid, i.e. methylated and non-methylated cytosines, whereby the nucleic acid is incubated in a solution comprising the nucleic acid for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid, i.e. the cytosine bases in the nucleic acid, are deaminated. Then the solution comprising the deaminated nucleic acid is desulfonated and preferably desalted. The application is further related to a solution comprising bisulfite with a certain pH and uses thereof as well as a kit comprising the solution.

6 Claims, 14 Drawing Sheets

OTHER PUBLICATIONS

Grigg, G., et al., 1994, "Sequencing 5-Methylcytosine Residues in Genomic DNA", *BioEssays*, 16(6):431436.

Grigg, G., 1996, "Sequencing 5-methylcytosine residues by the bisulphate method", *The Journal of Seq.&Mapping* 6:189-198.

Grunau, C., et al., 2001, "Bisulfite genomic sequencing: systematic investigation of critical experimental parameters", *Nucleic Acids Research*, 29 (13e65):1-7.

Guatelli, J., et al., 1990, "Isothermal, in vitro amplification of nucleic acids by a multienzyme reaction modeled after retroviral replication", *Proc. Natl. Acad. Sci. USA*, 87:1874-1878.

Hayatsu, H., et al., 1970, "The Addition of Sodium Bisulfite to Uracil and the Cytosine", *Journal of the American Chemical Society*, 92 (3):724-726.

Hayatsu, H., et al., 1970, "Reaction of Sodium Bisulfite with Uricil, Cytosine, and their Derivatives", *Biochemistry* 9 (14): 2858-2864.

Komlyama, M., et al., 1994, "Catalysis of Diethylenetriamine for Bisulfite-Induced Deamination of Cytosine in Oligodeoxyribonucleotides", *Tetrahedron Letters*, 35(44):8185-8188.

Kubareva, E., et al., 2002, Determination of Methylation Site of DNA-Methyltransferase *nla*X by a Hybrid Method', *BioTechniques* 33:526-531.

Kwoh, D., et al., 1989, "Transcription-based amplification system and detection of amplified human immunodeficiency virus type 1 with a bead-based sandwich hybridization format", *Proc. Natl. Acad. Sci. USA*, 86:1173-1177.

Oakeley, E., 1999, "DNA methylation analysis: a review of current methologies", *Pharmacology & Therapeutics*, 84:389-400.

Olek, A., et al., 1996, "A modified and improved method for bisulphate based cytosine methylation analysis", *Nucleic Acids Research*, 24(24):5064-5066.

Paulin, R., et al., 1998, "Urea improves efficiency of bisulphate-mediated sequencing of 5'-methylcytosine in genomic DNA", *Nucleic Acids Research*, 26(21):5009-5010.

Raizis, A., et al., 1995, "A Bisulfite method of 5-Methylcytosine Mapping That Minimizes Template Degradation", *Analytical Biochemistry*, 226:161-166.

Sabban, E., et al., 1982, The Effect of Bisulfite-induced C→U Transitions on Aminoacylation of *Escherichia coli* Glycine tRNA', *The Journal of Biological Chemistry*, 257 (9) 4796-4805.

Slae, S, et al., 1978, "Deamination of Cytidine by Bisulfite: Mechanism at Neutral pH", *J Org Chem.*, 43(21):497-4200

Whelen, A., et al., 1996, "The Role of Nucleic Acid Amplification and Detection in the Clinical Microbiology Laboratory", *Annu. Rev. Microbid*, 50:349-379.

Wu, D., et al., 1989, The Ligation Amplification Reaction (LAR)—Amplification of Specific DNA Sequences Using Sequential Rounds of Template-Dependent Ligation.

Fig. 1 Reaction of cytosines in nucleic acids with bisulfite

METHOD FOR BISULFITE TREATMENT

BACKGROUND OF THE INVENTION

This application claims the benefit of priority under 35 U.S.C. §119 of PCT/EP2004/000729 filed Jan. 28, 2004, and EP Application No. 03001854.3 filed Jan. 29, 2003 and EP Application 03010020.0 filed May 2003, the contents of which are hereby incorporated by reference.

FIELD OF THE INVENTION

The present application is directed to a method for performing a bisulfite reaction to determine methylation positions in a nucleic acid, i.e. methylated and non-methylated cytosines, whereby the nucleic acid is incubated in a solution comprising the nucleic acid for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid, i.e. the cytosine bases in the nucleic acid, is deaminated. Then the solution comprising the deaminated nucleic acid is desulfonated and preferably desalted. The application is further related to kit with a solution comprising bisulfite with a certain pH and uses thereof as well as a kit comprising the solution.

BACKGROUND OF THE INVENTION

Genes constitute only a small proportion of the total mammalian genome, and the precise control of their expression in the presence of an overwhelming background of noncoding deoxyribonucleic acid (DNA) presents a substantial problem for their regulation. Noncoding DNA, containing introns, repetitive elements, and potentially active transposable elements requires effective mechanisms for its long term silencing. Mammals appear to have taken advantage of the possibilities afforded by cytosine methylation to provide a heritable mechanism for altering DNA-protein interactions to assist in such silencing. DNA methylation is essential for the development of mammals and plays a potential role during aging and cancer. The involvement of methylation in the regulation of gene expression and as an epigenetic modification marking imprinted genes is well established. In mammals, methylation occurs only at cytosine residues and more specifically only on cytosine residues adjacent to a guanosine residue, i.e. at the sequence CG. The detection and mapping of DNA methylation sites are essential steps towards understanding the molecular signals which indicate whether a given sequence is methylated.

This is currently accomplished by the so-called bisulfite method described by Frommer, M., et al., Proc. Natl. Acad. Sci. USA 89 (1992) 1827-1831, for the detection of 5-methylcytosines. The bisulfite method of mapping 5-methylcytosine uses the effect that sodium hydrogen sulfite reacts with cytosine but not or only poorly with 5-methyl-cytosine. Cytosine reacts with bisulfite to form a sulfonated cytosine reaction intermediate being prone to deamination resulting in a sulfonated uracil which can be desulfonated to uracil under alkaline conditions (see FIG. 1). It is common knowledge that uracil has the base pairing behavior of thymine different to the educt cytosine whereas 5-methylcytosine has the base pairing behavior of cytosine. This makes the discrimination of methylated or non-methylated cytosines possible by e.g. bisulfite genomic sequencing (Grigg, G., and Clark, S., Bioessays 16 (1994) 431-436; Grigg, G. W., DNA Seq. 6 (1996) 189-198) or methylation specific PCR (MSP) disclosed in U.S. Pat. No. 5,786,146. Basic studies on the reaction of uracil and cytosine derivatives with bisulfite have been performed by Shapiro et al., JACS 92 (1970)422-424.

There are various documents addressing specific aspects of the bisulfite reaction.

Hayatsu, H., et al., Biochemistry 9 (1970) 2858-2865 reacted uracil, cytosine or their derivatives with 1 M bisulfite, at a pH value around 6, at 37° C. for 24 hours. Hayatsu, H., et al., J. Am. Chem. Soc. 92 (1970) 724-726 describe the reaction of cytosine with 3 M bisulfite at a pH value around 6 at a temperature of 80° C. for 30 min. Slae and Shapiro, J. Org. Chem. 43 (1978) 4197-4200 describe the deamination of cytidine with 1 M bisulfite around neutral pH at various temperatures whereby the reaction time is not described. There were no investigations of the deamination of cytosine or methyl-cytosine in nucleic acids in these documents.

Paulin, R., et al., Nucl. Acids Res. 26 (1998) 5009-5010 investigate the effects of urea on the efficiency of bisulfite-mediated sequencing of 5-methylcytosine in DNA. The DNA is reacted with 3.44 M bisulfite in the presence of 5.36 M urea and 0.5 mM hydroquinone, at a pH value of 5.0 at a temperature of 55° C. for 15 hours.

Raizis, A. M., et al., Anal. Biochem. 226 (1995) 161-166 disclose a bisulfite method for 5-methylcytosine mapping that minimizes template degradation. They investigate a method minimizing template degradation using 5 M bisulfite solutions in the presence of 100 mM hydroquinone at a pH value of 5 at 50° C. A maximum yield of PCR product was observed after 4 hours. Other conditions as increased pH and lower temperatures were also investigated.

Grunau, C., et al., Nucleic Acids Res 29 (2001) e65-5, page 1 to 7, perform a systematic investigation of critical experimental parameters of the bisulfite reaction. They investigate bisulfite solutions of 3.87 to 4.26 and 5.2 to 5.69 M at a pH value of 5. Temperatures that were tested are 15, 35, 55, 80, 85 and 95° C. for 1, 4 and 18 hours. DNA degradation is a problem in these investigations.

Wang, R. Y., et al., Nucleic Acids Res. 8 (1980) 4777-4790 disclose the use of a 3 M bisulfite solution at a pH value of 5.5 at a temperature of 37° C. for various time periods in the bisulfite treatment of DNA. Feil, R., et al., Nucleic Acids Res 22 (1994) 695-696 disclose the use of a 3.5 M bisulfite solution at a pH value of 5 at a temperature of 0° C. for 24 hours in the bisulfite treatment of DNA. Clark, S. J., et al., Nucleic Acids Res 22 (1994) 2990-2997, disclose the use of a 3 to 4 M bisulfite solution at a pH value of 4.8 to 5.8 at a temperature of 37 to 72° C. for 8 to 16 hours in the bisulfite treatment of DNA. Tasheva, E. S., and Roufa, D. J., Mol. Cell. Biol. 14 (1994) 5636-5644 disclose the use of a 1 M bisulfite solution at a pH value of 5 at a temperature of 50° C. for 48 hours in the bisulfite treatment of fragments of genomic DNA. Grigg, G. W., DNA Seq 6 (1996) 189-198 discloses the use of a 3.1 M bisulfite solution at a pH value of 5 at a temperature of 50° C. for 16 hours in the bisulfite treatment of DNA. Komiyama, M., and Oshima, S., Tetrahedron Letters 35 (1994) 8185-8188 disclose the use of a 1 M bisulfite solution at a pH value of 5 at a temperature of 37° C. for 4 hours in the bisulfite treatment of DNA whereby diethylenetriamine is present.

Olek, A., et al., Nucleic Acids Res. 24 (1996) 5064-5066 disclose a method for bisulfite base sequencing whereby bisulfite treatment and subsequent PCR steps are performed on material embedded in agarose beads. A 5 M bisulfite solution at a pH value of 5 at a temperature of 50° C. is used for 4 hours in the bisulfite treatment of DNA.

A review of DNA methylation analysis can be found in Oakeley, E. J., Pharmacol. Ther. 84 (1999) 389-400.

Different additional components in the bisulfite mixture are disclosed by WO 01/98528, WO02/31186 or by Paulin, R., et al., Nucleic Acids Res 26 (1998) 5009-5010.

Kits for performing bisulfite treatments are commercially available from Intergen, now distributed by Serologicals Corporation, Norcross, Ga., USA, e.g. CpGenome™ DNA modification kit (http://www.serologicals.com/products/int_prod/index.html).

All prior art methods for the bisulfite treatment have disadvantages. Therefore, the problem to be solved by the present invention was to provide a method which overcomes the disadvantages of the prior art methods.

SUMMARY OF THE INVENTION

The present invention provides a method for the conversion of a cytosine base, preferably cytosine bases, in a nucleic acid to an uracil base, preferably cytosine bases, whereby preferably a 5-methyl-cytosine base, preferably 5-methyl-cytosine bases, is not significantly converted, comprising the steps of
a) incubating a solution comprising the nucleic acid for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid is deaminated, and
b) incubating the solution comprising the deaminated nucleic acid under alkaline conditions whereby the deaminated nucleic acid is desulfonated.

Further, the invention provides a solution with a pH value between 5.0 and 6.0 and comprising bisulfite in a concentration between 3 M and 6.25 M, uses thereof and kits comprising this solution.

As known to the expert skilled in the art and according to the invention, the term "bisulfite" is used interchangeably for "hydrogensulfite".

According to the invention the term a "bisulfite reaction", "bisulfite treatment" or "bisulfite method" shall mean a reaction for the conversion of a cytosine base, preferably cytosine bases, in a nucleic acid to an uracil base, preferably uracil bases, in the presence of bisulfite ions whereby preferably a 5-methyl-cytosine base, preferably 5-methyl-cytosine bases, is not significantly converted. This reaction for the detection of methylated cytosines is described in detail by Frommer et al., supra and Grigg and Clark, supra. The bisulfite reaction contains a deamination step and a desulfonation step which can be conducted separately or simultaneously (see FIG. 1; Grigg and Clark, supra). The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases (Frommer et al., supra). The expert skilled in the art knows how to perform the bisulfite reaction, e.g. by referring to Frommer et al., supra or Grigg and Clark, supra who disclose the principal parameters of the bisulfite reaction. From Grunau et al., supra, it is known to the expert in the field what variations of the bisulfite method are possible. In summary, in the deamination step a buffer containing bisulfite ions, optionally chaotropic agents and optionally further reagents as an alcohol or stabilizers as hydroquinone are employed and the pH is in the acidic range. The concentration of bisulfite is between 0.1 and 6 M bisulfite, preferably between 1 M and 5.5 M, the concentration of the chaotropic agent is between 1 and 8 M, whereby preferably guanidinium salts are employed, the pH is in the acidic range, preferably between 4.5 and 6.5, the temperature is between 0° C. and 90° C., preferably between room temperature (25° C.) and 90° C., and the reaction time is between 30 min and 24 hours or 48 hours or even longer, but preferably between 1 hour and 24 hours. The desulfonation step is performed by adding an alkaline solution or buffer as e.g. a solution only containing a hydroxide, e.g sodium hydroxide, or a solution containing ethanol, sodium chloride and sodium hydroxide (e.g. 38% EtOH, 100 mM NaCl, 200 mM NaOH) and incubating at room temperature or elevated temperatures for several min, preferably between 5 min and 60 min.

The method according to the invention allows a relatively short reaction time of the bisulfite reaction giving the possibility to perform a DNA assay within one working day. One parameter to speed the reaction is the temperature. To decrease the DNA degradation process, a low pH value is of advantage. By the use of a 5 M bisulfite solution of a pH value of 5.5 at a temperature of approximately 80° C., a reaction time of e.g. between 120 and 180 min is possible. Further, the reaction under conditions according to the invention is more specific for cytosine compared to 5-methylcytosine as with standard conditions after 16 h. Additives for stabilization of the bisulfite reagent like hydroquinone are possible.

DETAILED DESCRIPTION OF THE INVENTION

The invention is related to a method for the conversion of a cytosine base, preferably cytosine bases in a nucleic acid to an uracil base, preferably uracil bases, whereby preferably a 5-methyl-cytosine base, preferably 5-methyl-cytosine bases, is not significantly converted, comprising the steps of
a) incubating a solution comprising the nucleic acid for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid is deaminated, and
b) incubating the solution comprising the deaminated nucleic acid under alkaline conditions whereby the deaminated nucleic acid is desulfonated.

In a preferred embodiment of the invention, the method may further comprise the step of desalting the solution comprising the deaminated and desulfonated nucleic acid. This can be achieved e.g. by ultrafiltration, gel filtration, precipiation as known to the expert skilled in the art or by binding to magnetic glass particles as described in WO 96/41811.

In a preferred embodiment of the invention, the temperature in the method according to the invention is between 75 and 85° C. In another preferred embodiment of the invention, the concentration of bisulfite is between 3.2 M and 6 M, preferably between 4.75 M and 5.5 M. In another preferred embodiment of the invention, the pH value of the solution is between 5.25 and 5.75. In another preferred embodiment of the invention, the time period is between 1.75 and 3 hours. In another preferred embodiment of the invention, the time period is between 2 and 3 hours, preferably between 2 and 2.5 hours. The reaction is also possible in a time period between 0.75 and 3.5 hours. In the most preferred embodiment of the invention, in step a) the temperature is 80° C., the concentration of bisulfite is 5 M, the pH value of the solution is 5.5 and the time period is preferably between 2 and 2.5 or 3 hours, most preferred 2 hours.

The method is preferably performed in solution, however, it is also feasible that the method according to the invention is performed while the nucleic acid is in a solid phase bound form, i.e. it is bound to a solid phase under suitable conditions. The solid phase may be a silicon oxide, preferably in the form of glass fleeces or fibers or magnetic glass particles as described in WO96/41811, WO 00/32762 and WO 01/37291. The principal method of performing a bisulfite treatment while the nucleic acid is bound to a solid phase is e.g. described e.g. in the European patent application with the number EP 02 019 097.1 and EP 02 028 114.3.

The expert skilled in the art knows how to perform the bisulfite reaction, e.g. by referring to Frommer et al., supra, Grigg and Clark, supra or Grunau et al., supra who disclose the principal parameters of the bisulfite reaction.

In an embodiment of the invention, the nucleic acid is deoxyribonucleic acid (DNA), in particular genomic DNA or nucleic acid, i.e. the DNA or nucleic acid which is found in the organism's genome and is passed on to offspring as information necessary for survival. The phrase is used to distinguish between other types of DNA, such as found within plasmids. The source of the nucleic acid may be eukaryotic or prokaryotic, preferably from vertebrates, particularly from mammalians, most preferred from animals or humans.

In an embodiment of the invention the nucleic acid is obtained from a biological sample using the solid phases as described above and methods known to the expert in the field. The biological sample comprises cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body. The biological sample can be blood, blood plasma, blood serum, tissue or urine. The biological sample comprising the nucleic acids is lysed to create a mixture of biological compounds comprising nucleic acids and other components. Procedures for lysing biological samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook, J., et al., in "Molecular Cloning: A Laboratory Manual" (1989), eds. J. Sambrook, E. F. Fritsch and T. Maniatis, Cold Spring Harbour Laboratory Press, Cold Spring Harbour, N.Y.; and Ausubel, F., et al., in "Current protocols in molecular biology" (1994), eds. F. Ausubel, R. Brent and K. R. E., Wiley & Sons, New York. Then the nucleic acids are isolated from the lysis mixture using the methods known to the expert skilled in the art, e.g. using solid phases as magnetic glass particles (WO96/41811), and can then be subjected to the methods according to the invention, i.e. the bisulfite treatment according to the invention. Chaotropic agents are also used to lyse cells to prepare a mixture between nucleic acids and other biological substances (see e.g. Sambrook et al. (1989) or EP 0 389 063). Afterwards a material comprising glass or silica may be added and a purification effect results from the behavior of DNA or RNA to bind to material with a glass surface under these conditions i.e. in the presence of certain concentrations of a chaotropic agent, higher concentrations of organic solvents or under acidic conditions. Sequence specific capturing can also be used for this purpose.

In a preferred embodiment of the invention, the nucleic acid is amplified after the steps of the method according to the invention with the polymerase chain reaction (PCR: EP 0 201 184; EP-A-0 200 362; U.S. Pat. No. 4,683,202). The amplification method may also be the Ligase Chain Reaction (LCR: Wu, D. Y., and Wallace, R. B., Genomics 4 (1989) 560-569; and Barany, P., Proc. Natl. Acad. Sci. USA 88 (1991) 189-193), Polymerase Ligase Chain Reaction (Barany, F., PCR Methods Appl. 1 (1991) 5-16), Gap-LCR (PCT Patent Publication No. WO 90/01069), Repair Chain Reaction (European Patent Publication No. EP-A 0 439 182), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; PCT Patent Publication No. WO 92/0880A), and NASBA (U.S. Pat. No. 5,130,238). Further, there are strand displacement amplification (SDA), transcription mediated amplification (TMA), and Q□-amplification (for a review see e.g. Whelen, A. C., and Persing, D. H., Annu. Rev. Microbiol. 50 (1996) 349-373; Abramson, R. D., and Myers, T. W., Curr. Opin. Biotechnol. 4 (1993) 41-47). Particularly preferred amplification methods according to the invention are the methylation specific PCR method (MSP) disclosed in U.S. Pat. No. 5,786,146 which combines bisulfite treatment and allele-specific PCR (see e.g. U.S. Pat. No. 5,137,806, U.S. Pat. No. 5,595,890, U.S. Pat. No. 5,639,611).

In a preferred embodiment, the method may further comprise the step of detecting the amplified nucleic acid. The amplified nucleic acid may be determined or detected by standard analytical methods known to the person skilled in the art and described e.g. by Sambrook, J., et al., in "Molecular Cloning: A Laboratory Manual" (1989), eds. J. Sambrook, E. F. Fritsch and T. Maniatis, Cold Spring Harbor Laboratory Press, Cold Spring Harbor, N.Y.; Lottspeich and Zorbas, in "Bioanalytik" (1998), eds. L. a. Zorbas, Spektrum Akademischer Verlag, Heidelberg, Berlin, Germany; or by Ausubel, F., et al., in "Current protocols in molecular biology" (1994), eds. F. Ausubel, R. Brent and K. R. E., Wiley & Sons Verlag, New York. There may be also further purification steps before the target nucleic acid is detected e.g. a precipitation step. The detection methods may include but are not limited to the binding or intercalating of specific dyes as ethidium bromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridisation to specific sequences and subsequent detection of the hybrid. It is also possible to sequence the target nucleic acid after further steps known to the expert in the field. Other methods apply a diversity of nucleic acid sequences to a silicon chip to which specific probes are bound and yield a signal when a complementary sequence binds.

In a particularly preferred embodiment of the invention, the nucleic acid is detected by measuring the intensity of fluorescence light during amplification. This method entails the monitoring of real time fluorescence. A particularly preferred method exploiting simultaneous amplification and detection by measuring the intensity of fluorescent light is the TaqMan® method disclosed in WO 92/02638 and the corresponding U.S. Pat. No. 5,210,015, U.S. Pat. No. 5,804,375, U.S. Pat. No. 5,487,972. This method exploits the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TaqMan® technology eliminates the need for a solid phase bound reaction complex to be formed and made detectable. In more general terms, the amplification and/or detection reaction of the method according to the invention is a homogeneous solution-phase assay. Further preferred methods are the formats used in the Light-Cycler® instrument (see e.g. U.S. Pat. No. 6,174,670). Particularly preferred is the use of bisulfite treatment, amplification with or without methylation specific primers in the presence of a methylation-specific probe and real-time fluorescence detection as described in U.S. Pat. No. 6,331,393.

In a preferred embodiment of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In a preferred embodiment of the invention, the method is in a high-throughput format, i.e. the automated methods is carried out in a high-throughput format which means that the methods and the used machine or apparatus are optimized for a high-throughput of samples in a short time.

Preferably, the method according to the invention is used in diagnostics, for diagnostic analysis or for bioanalytics, or for the screening of tissue or fluids from the human or even animal body for the presence of a certain methylation pattern. Further, the method according to the invention is used to enhance the speed, accuracy or sensitivity of the detection of methylation sites in nucleic acids.

In another embodiment of the invention, a solution with a pH value between 5.0 and 6.0 and comprising bisulfite in a concentration between 3 M and 6.25 M is used in a reaction at a reaction temperature between 70 and 90° C. wherein a cytosine base, preferably cytosine bases, in a nucleic acid are converted to an uracil base, preferably uracil bases, in the presence of bisulfite ions whereby preferably a 5-methyl-cytosine base, preferably 5-methyl-cytosine bases, is not significantly converted. Preferably, the pH value of the solution is between 5.25 and 5.75 and the concentration of bisulfite is between 3.2 M and 6 M, preferably between 4.75 M and 5.5 M. In the most preferred embodiment, the pH value of the solution is 5.5 and the concentration of bisulfite is 5 M. The solution may also contain hydroquinone for stabilisation. The solution according to the invention is preferably an aqueous solution. Preferably, the reaction temperature is between 75 and 85° C.

In another embodiment of the invention a kit comprising a solution according to the invention. Preferably, The solution has a pH value between 5.25 and 5.75, more preferably between 5.4 and 5.6, and comprises bisulfite in a concentration between 3 M and 6.25 M. Preferably, the concentration of bisulfite is between 3.5 M and 6 M, preferably between 4.75 M and 5.5 M. The solution may optionally contain hydroquinone. In the most preferred embodiment, the pH value of the solution is 5.5 and the concentration of bisulfite is 5 M. Such kits known in the art further comprise plastics ware which may be used during the bisulfite procedure as e.g. microtiter-plates in the 96 or 384 well format or reaction tubes manufactured e.g. by Eppendorf, Hamburg, Germany. The kit may further comprise a washing solution which is suitable for the washing step of the solid phase, in particular, the glass fleece or membrane or the magnetic glass particles. Often the washing solution is provided as a stock solution which has to be diluted before the use. The kit may further comprise an eluent, i.e. a solution or a buffer (e.g. TE, 10 mM Tris, 1 mM EDTA, pH 8.0) or pure water to elute the DNA or RNA bound to the solid phase. Further, additional reagents may be present which contain buffers suitable for use in the present invention. Preferably, the kit according to the invention is used for a reaction wherein a cytosine base, preferably cytosine bases, in a nucleic acid are converted to an uracil base, preferably uracil bases, in the presence of bisulfite ions whereby preferably a 5-methyl-cytosine base, preferably 5-methyl-cytosine bases, are not significantly converted.

In another embodiment of the invention, a solution is provided with a pH value between 5.4 and 5.6 and comprising bisulfite in a concentration between 3.5 M and 6.25 M. The solution optionally contains hydroquinone or other radical scavengers. Preferably, the concentration of bisulfite is between 3.75 M and 6 M, preferably between 4.75 M and 5.5 M. In the most preferred embodiment, the pH value of the solution is 5.5 and the concentration of bisulfite is 5 M.

The following examples, references, sequence listing and figures are provided to aid the understanding of the present invention, the true scope of which is set forth in the appended claims. It is understood that modifications can be made in the procedures set forth without departing from the spirit of the invention.

Figure 1:
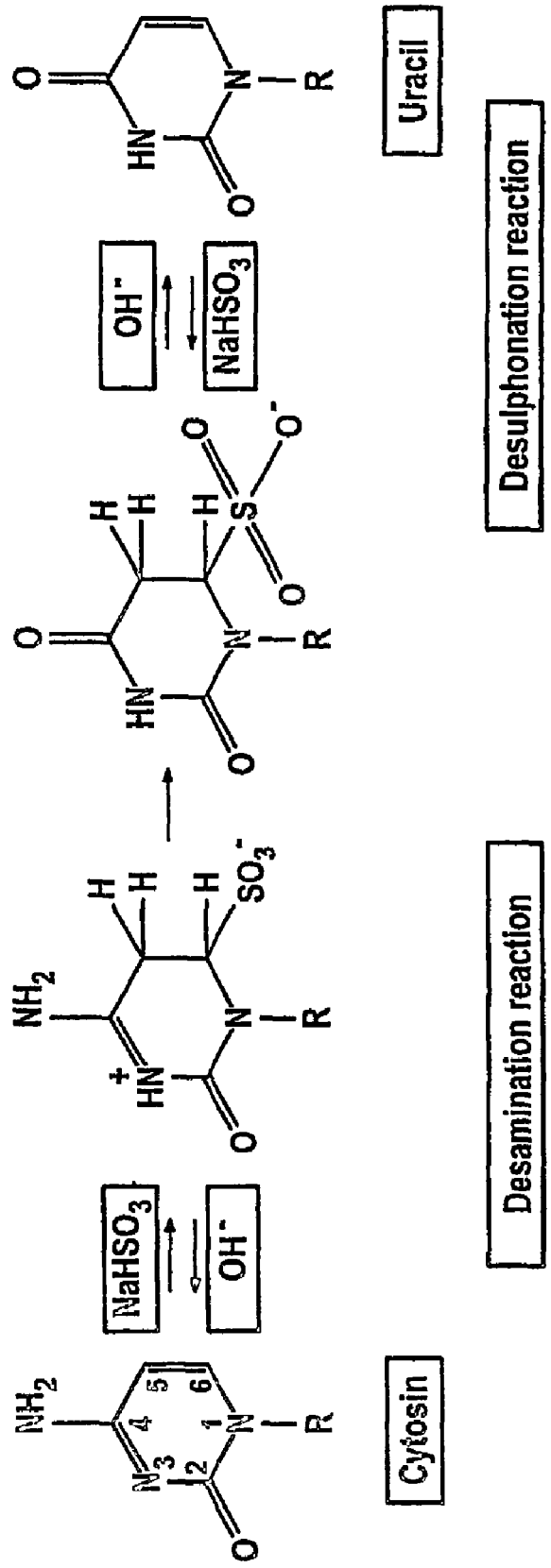
FIG. 1: The steps of the bisulfite method
Figure 2:
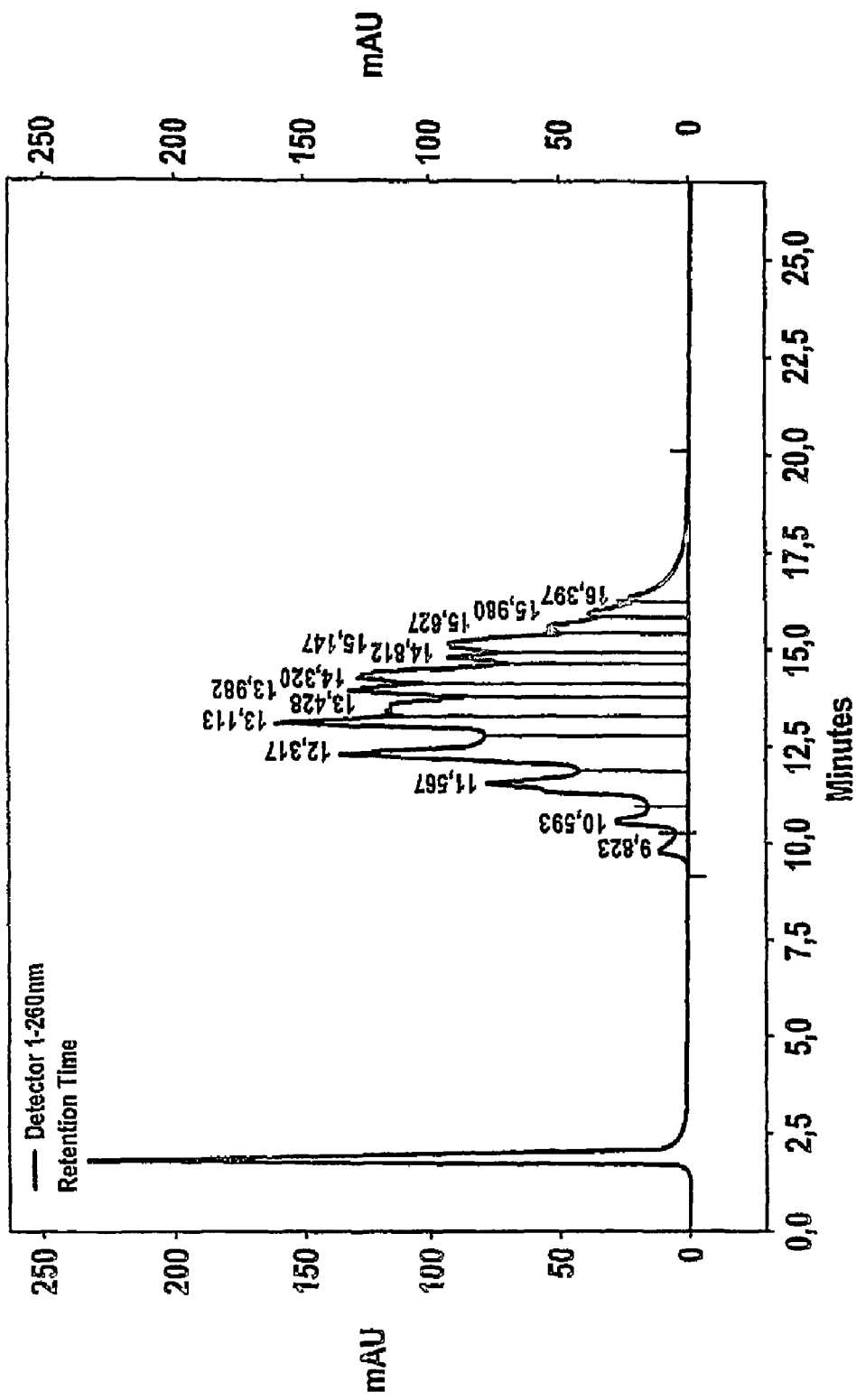
FIG. 2 to 14: HPLC profiles of the reaction mixtures after certain time periods as indicated in the examples
Figure 3:
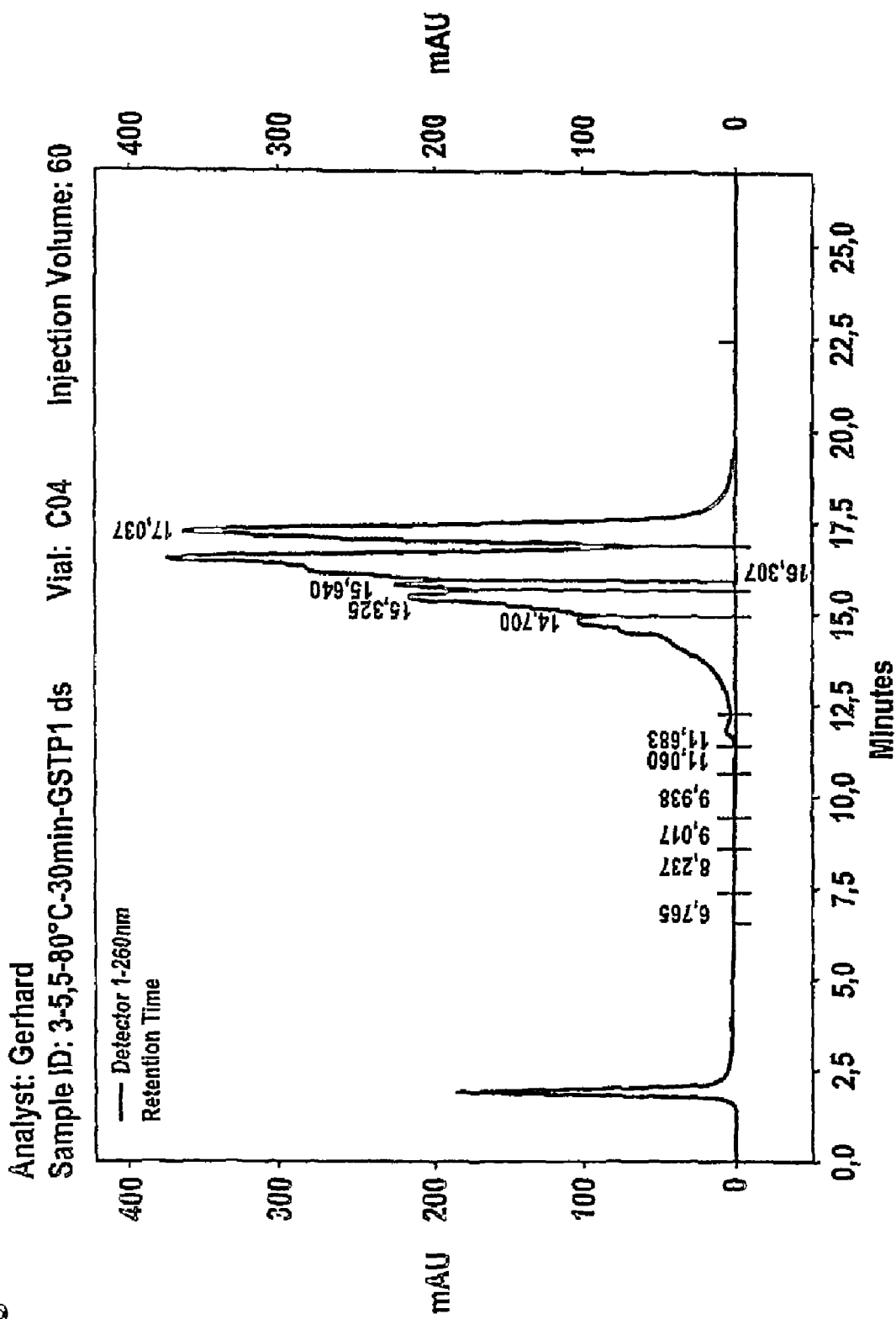
Figure 4:
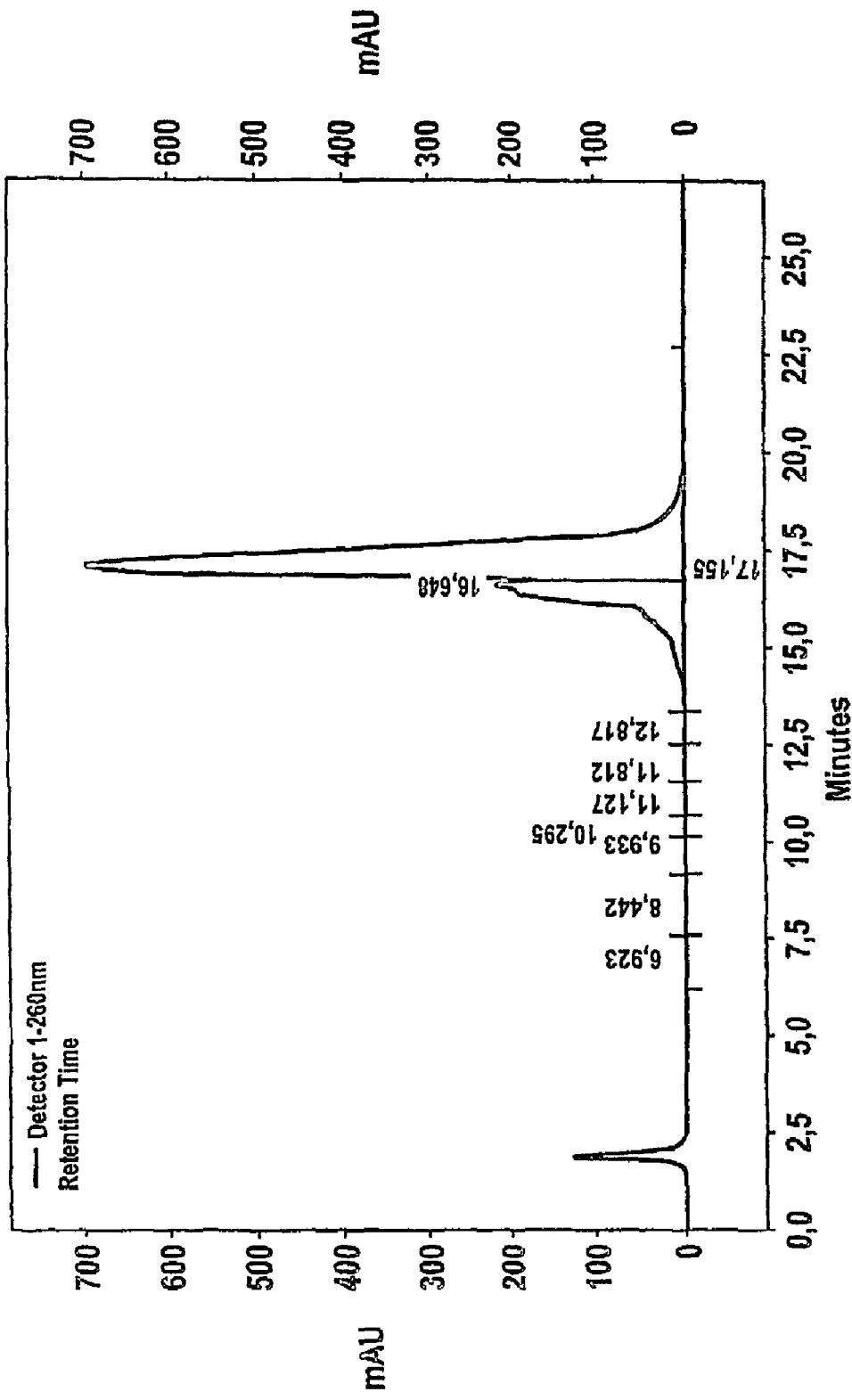
Figure 5:
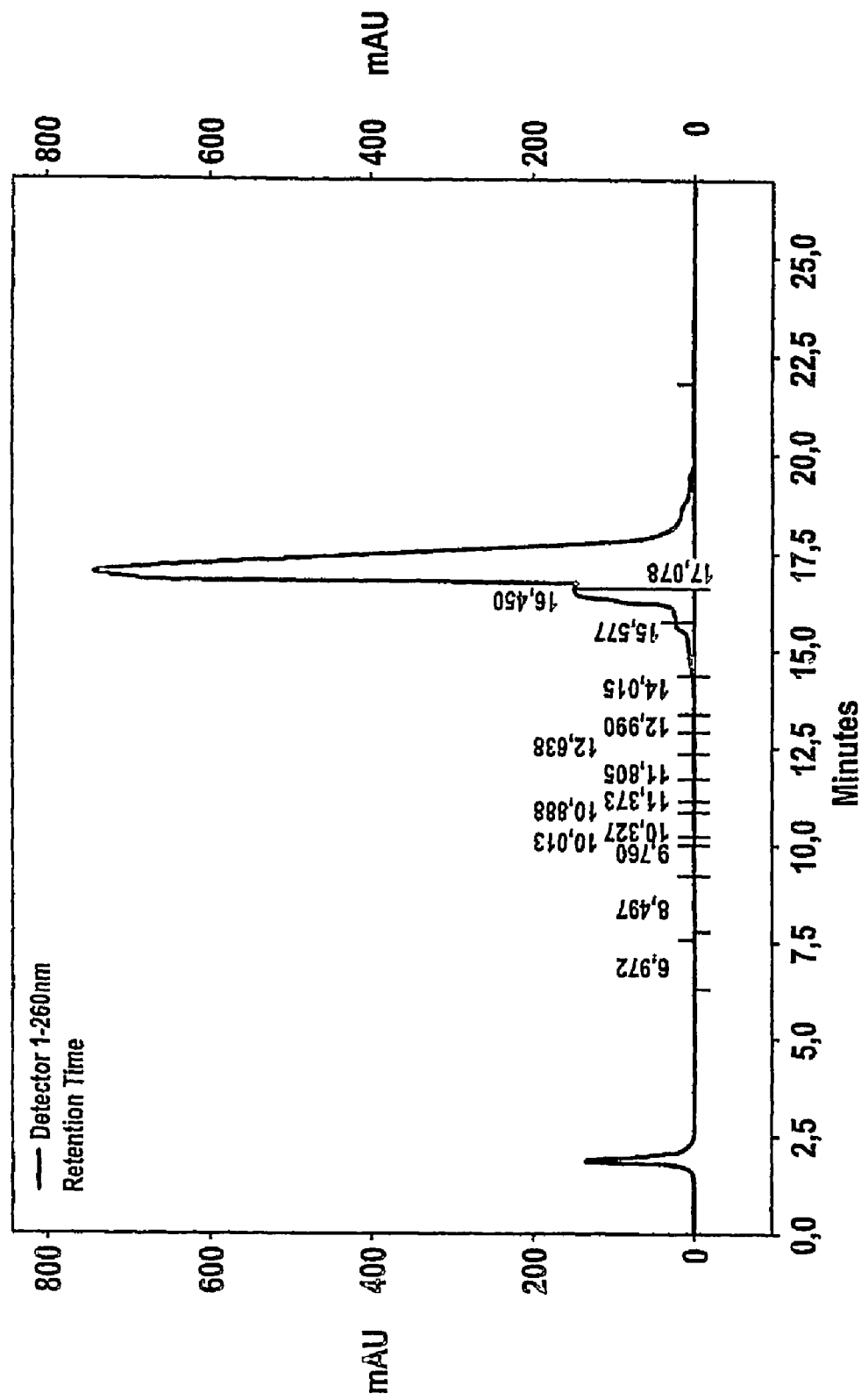
Figure 6:
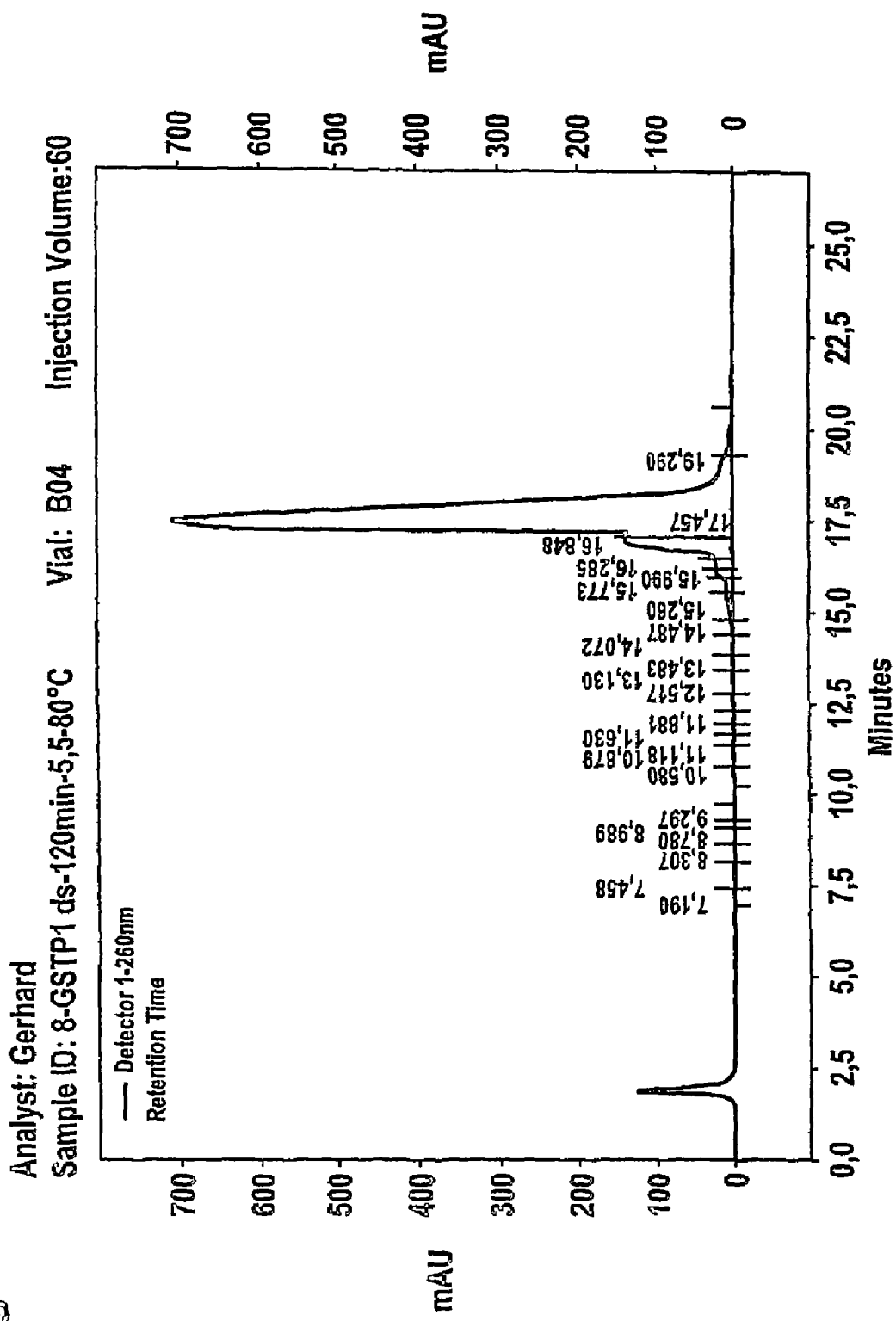
Figure 7:
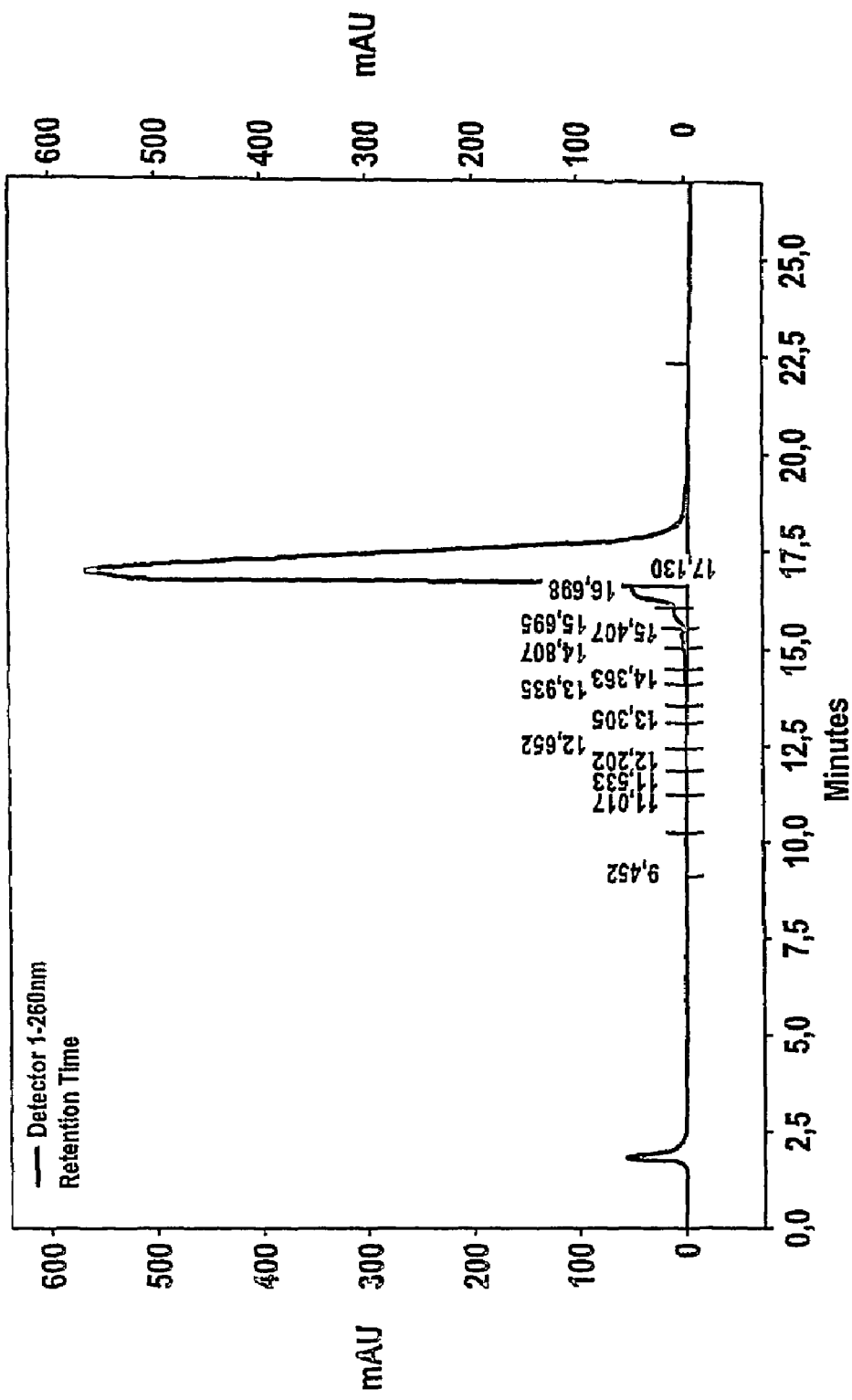
Figure 8:
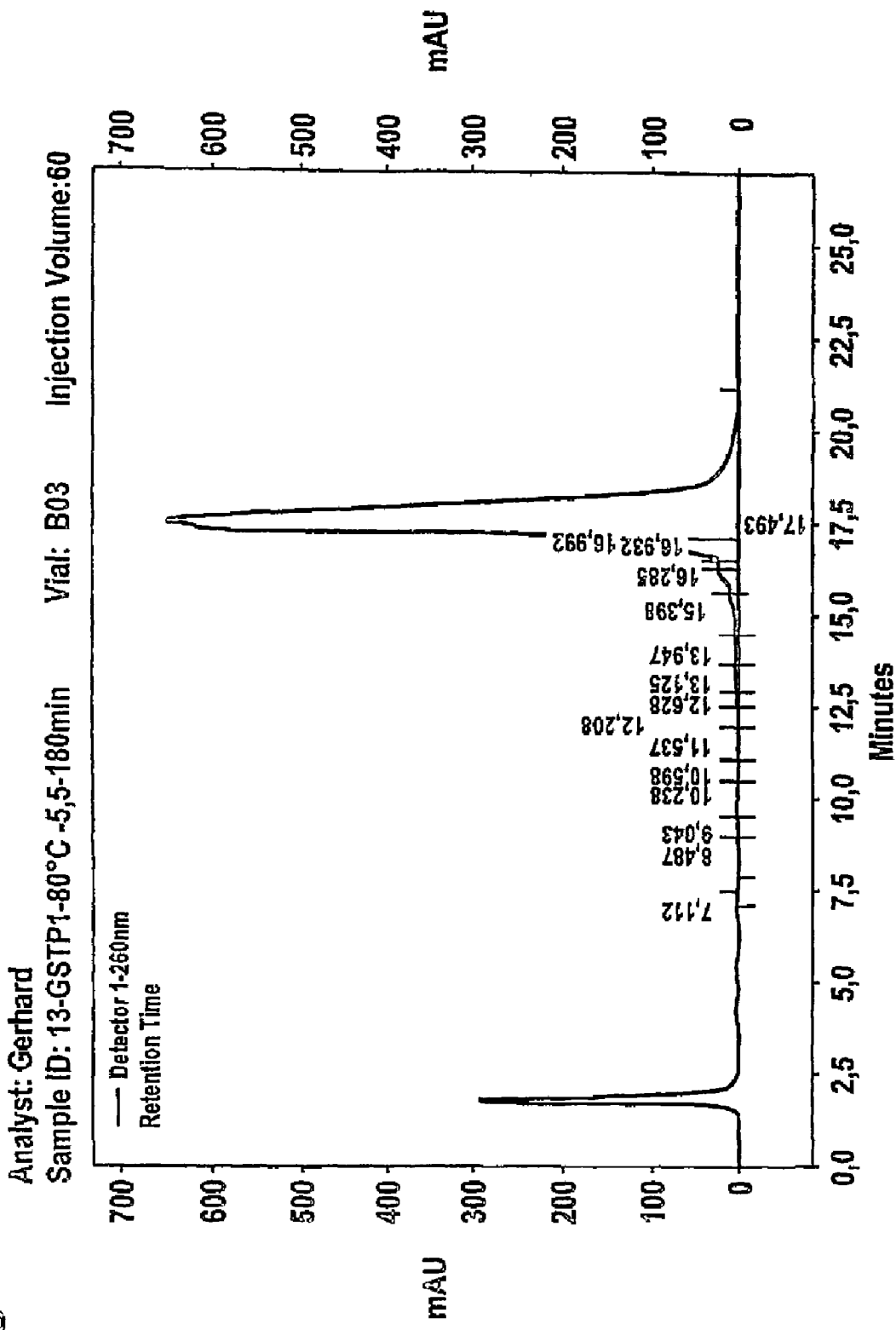
Figure 9:
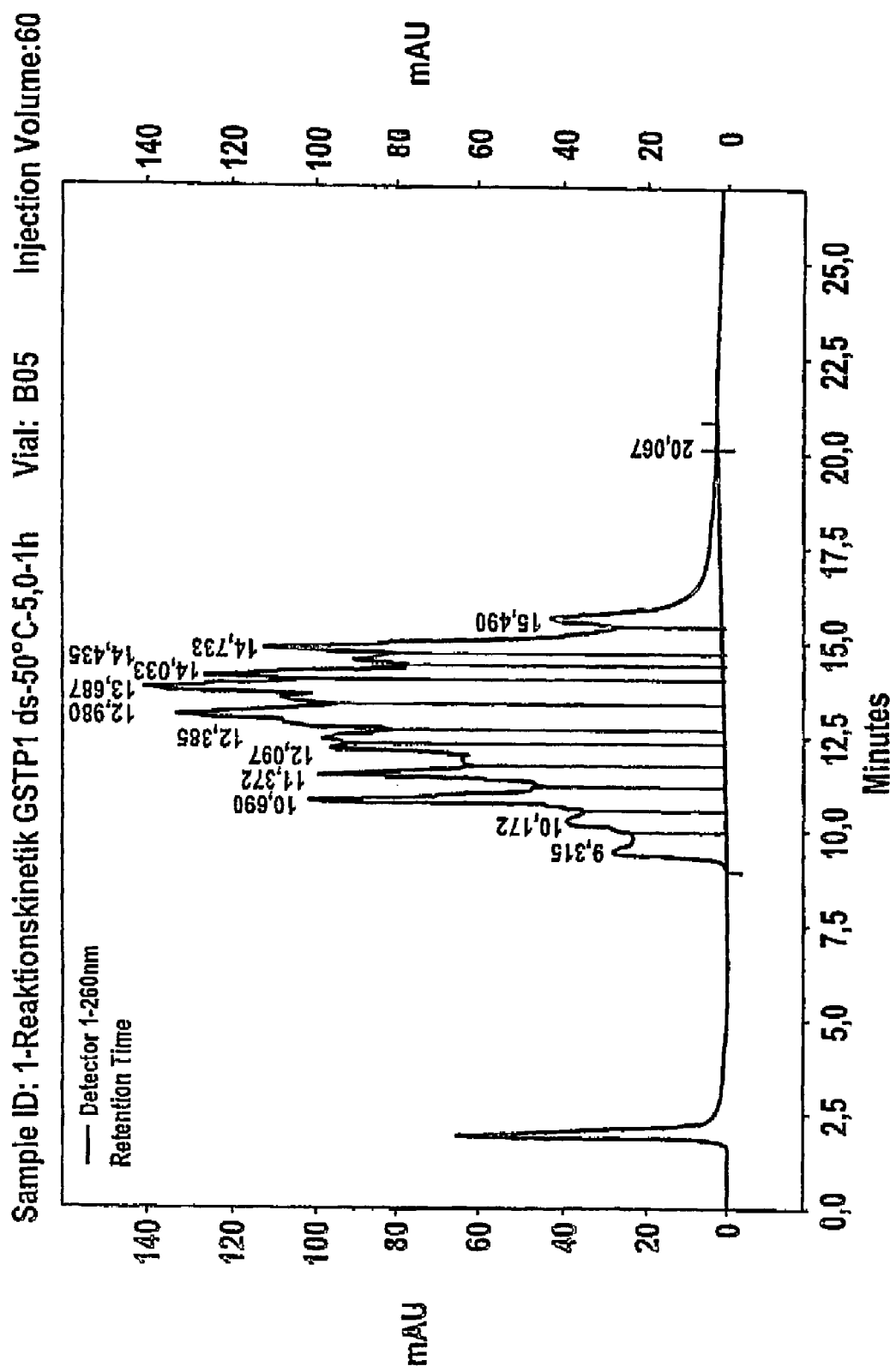
Figure 10:
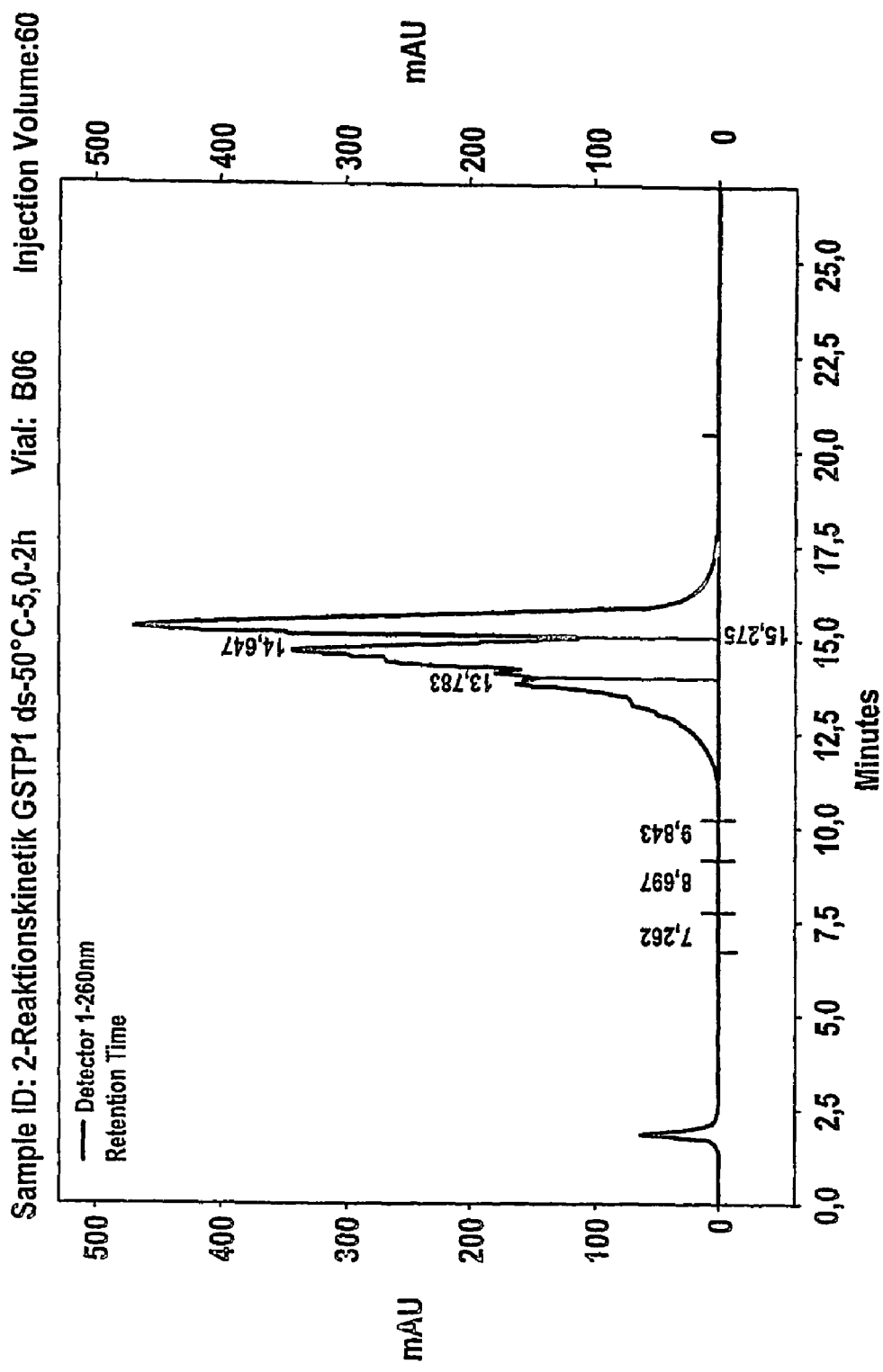
Figure 11:
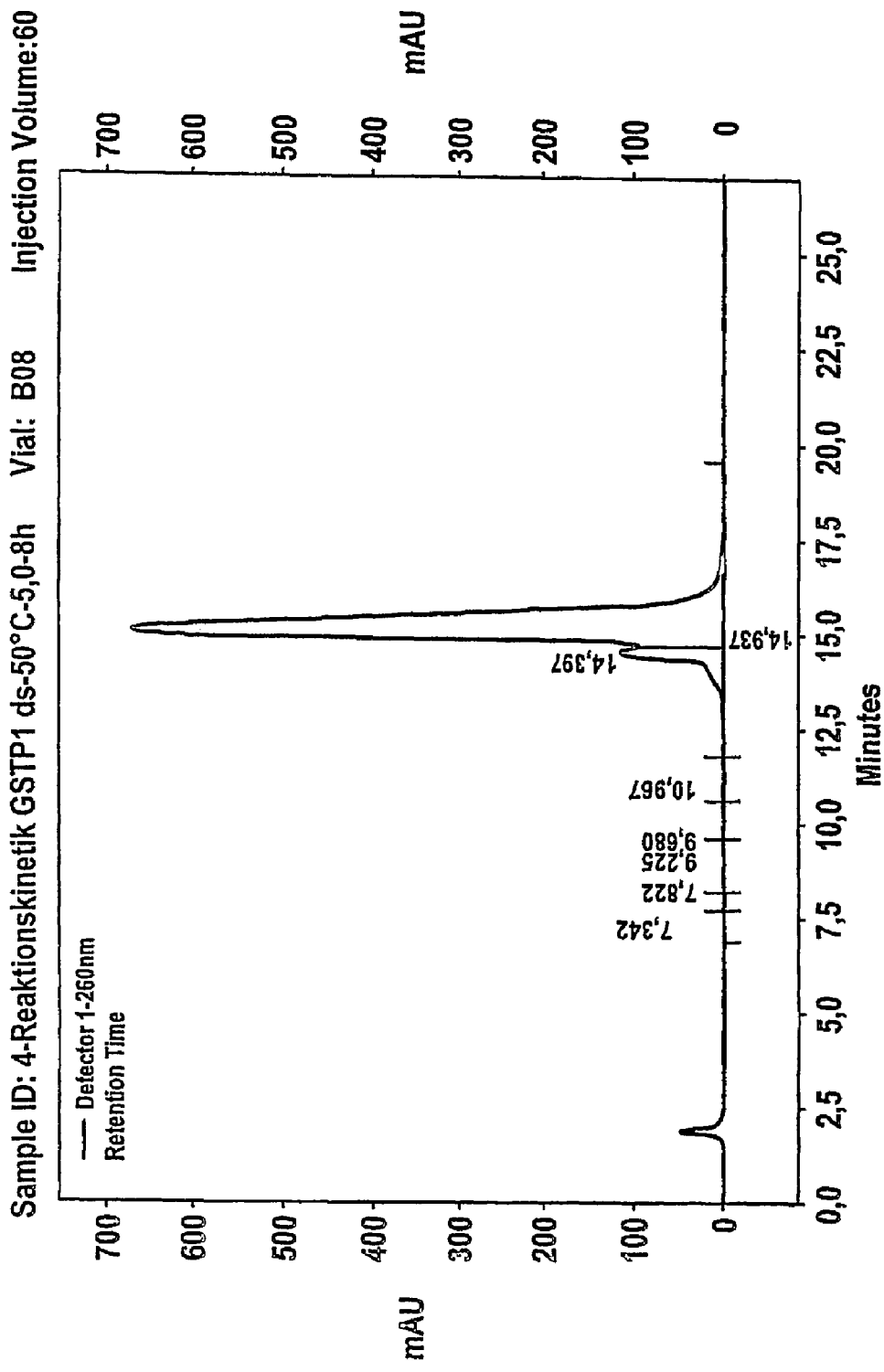
Figure 12:
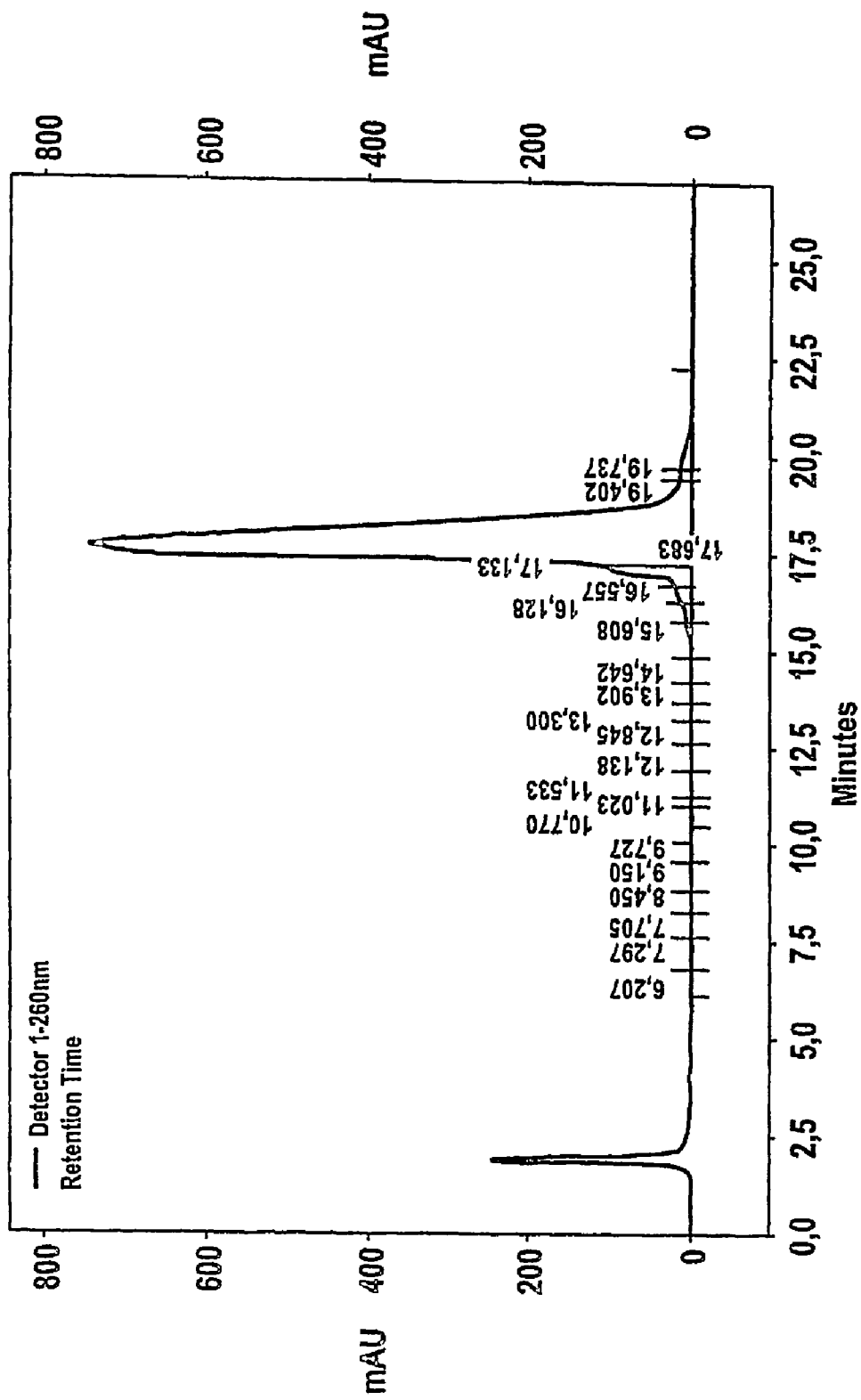

1 EXAMPLES 1.1 Comparison Optimized Conditions with Standard Conditions Using a Model System (Oligonucleotide) and Analysis by HPLC 1.1.1 Method:
1.1.1.1 Composition of Reagents

| | |
|---|---|
| Bisulfite reagent pH = 5,0/50° C.: ("Standard") | 1,9 g $Na_2S_2O_5$<br>2 ml Millipore water<br>0,7 ml 2M NaOH<br>0,5 ml 1M hydroquinone (optional)<br>addition of Millipore water to a volume of 4 ml |
| Bisulfite reagent pH = 5,5/80° C.: | 1,9 g $Na_2S_2O_5$<br>1 ml Millipore water<br>2 ml 2M NaOH |

-continued

| | 0,5 ml 1M hydroquinone (optional) addition of Millipore water to a volume of 4 ml |
|---|---|

Hydroquinone can be added optionally; it is not necessary if the reagent is prepared freshly for the experiment.

Sequences:

The oligonucleotides are synthesized using standard automated solid-phase synthesis procedure applying phosphoramidite chemistry.

GSTP1 Sequence:

SEQ ID NO:1:  5'-d(GAGGGGCGCCCTGGAGTCCC)-3' (sense strand)

SEQ ID NO:2:  5'-d(GGGACTCCAGGGCGCCCCTC)-3' (antisense strand)

SEQ ID NO:3:  5'-d(GAGGGGUGUUUTGGAGTUUU)-3' (sense strand C converted to U (product))

SEQ ID NO:4:  5'-d(GGGAUTUUAGGGUGUUUUTU)-3' (antisense strand C converted to U (product))

C or $C^{Me}$ in the Center Position of $T_{10}$:

SEQ ID NO:5:  5'-d($T_5CT_5$)-3'

SEQ ID NO:6:  5'-d($T_5C^{Me}T_5$)-3'

SEQ ID NO:7:  5'-d($T_5UT_5$)-3'

SEQ ID NO:8:  5'-d($T_{11}$)-3'

1.1.1.2 Reaction Conditions:

Ca. 5 nmole of a single stranded oligonucleotide or 5 nmole of each strand of a double stranded oligonucleotide are dissolved in 20 µl of Millipore water, then 200 µl of the bisulfite reagent are added. Thereafter the reaction tube is placed into a thermomixer (50° C. or 80° C.; 600 rpm). After t=x hours the reaction is stopped by addition of 500 µl of 2.5M NaOH (desulfonation). After 30 min at r.t. the reaction mixture is desalted over a Sephadex G25 column. The oligonucleotide containing fraction is evaporated and dissolved in 200 µl of Millipore water to be analyzed by HPLC.

| | Evaluation | |
|---|---|---|
| Analytical HPLC: | column: | Dionex DNA Pac PA-100 SEL |
| | buffer A: | 0,01 M NaOH, 0,2 M NaCl |
| | buffer B: | 0,01 M NaOH, 1M NaCl |
| | gradient: | 50-100% B in 25 min |

Data evaluation: HPLC chromatograms are compared by HPLC-area % of the product peak at t=x and are shown in FIGS. 2 to 12

1.1.2 Results 1.1.2.1 Reaction Kinetics GSTP1 ds at T=80° C., pH=5.5

A double determination was performed according to the standard protocol described above with the GSTP1 sequences SEQ ID NO:1 which is the sense strand and SEQ ID NO:2 which is the antisense strand, the mean average values are calculated.

| t[min] | HPLC area % product | FIG. |
|---|---|---|
| 10 | 0 | 2 |
| 30 | 27,0 | 3 |
| 60 | 77,5 | 4 |
| 90 | 87,5 | 5 |
| 120 | 89,9 | 6 |
| 150 | 90,4 | 7 |
| 180 | 88,6 | 8 |

1.1.2.2 Reaction Kinetics GSTP1 ds at T=50° C., pH=5.0 ("Standard Conditions")

A double determination was performed according to the standard protocol described above with the GSTP1 sequences SEQ ID NO:1 which is the sense strand and SEQ ID NO:2 which is the antisense strand, the mean average values are calculated.

| t[h] | HPLC area % product | FIG. |
|---|---|---|
| 1 | 15,6 | 9 |
| 2 | 41,2 | 10 |
| 4 | 72,5 | |
| 8 | 89,4 | 11 |
| 16 | 91,8 | 12 |
| 20 | 85,0 | |

1.1.2.3. Specificity of Bisulfite Reaction T5CMeT5 at T=80° C., pH=5.5 (Optimized Conditions) Compared to "Standard Conditions" at T=50° C., pH=5.0

Figure 13:
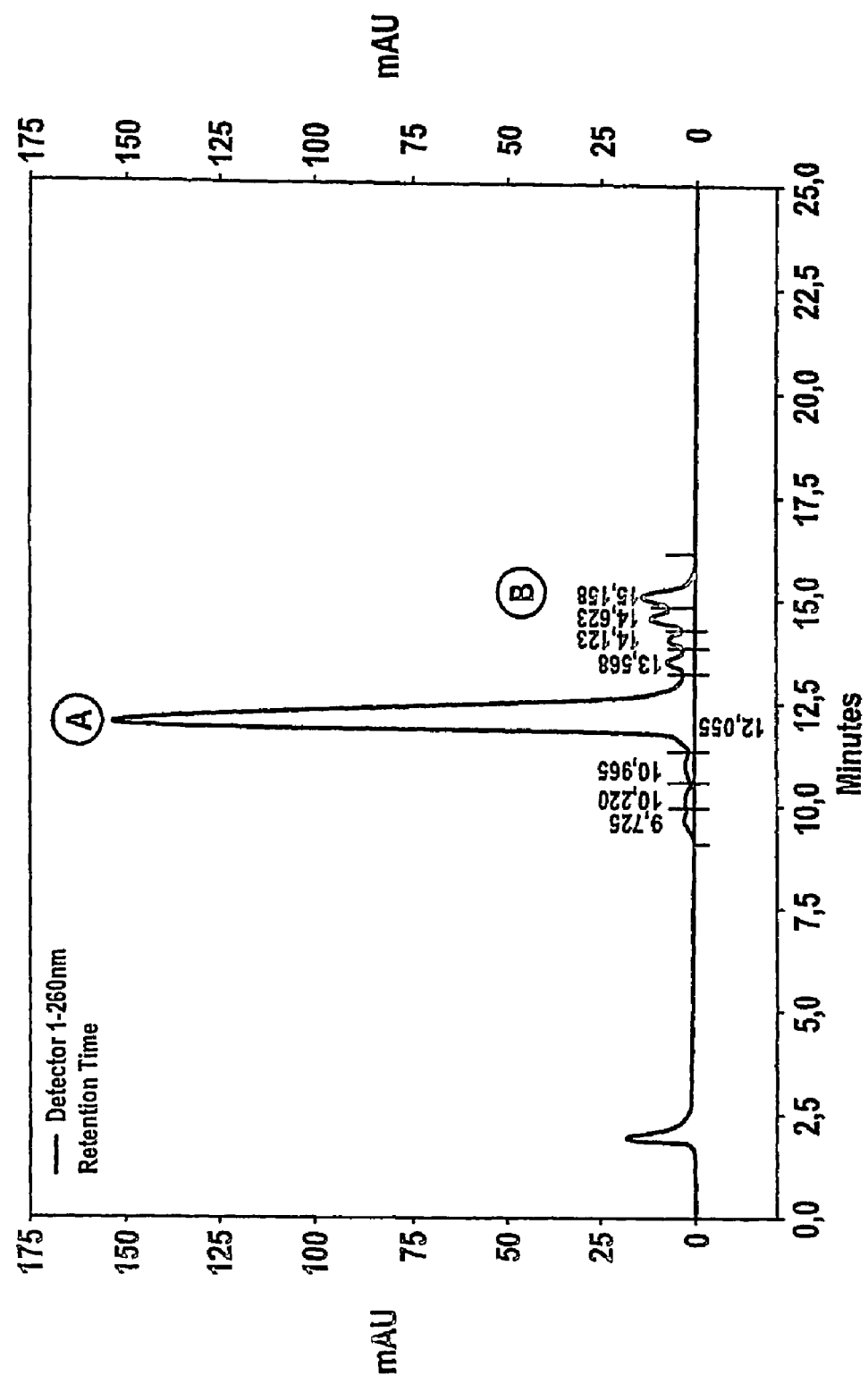

In order to evaluate the specificity of bisulfite reaction, the oligonucleotide 5'-$T_5C^{Me}T_5$-3' (SEQ ID NO: 6) was evaluated under the indicated conditions. The results were as follows:

5 M bisulfite pH 5.0 T=50° C./t=16 h (standard conditions) (see FIG. 13 for an exemplary chromatogram):

| sample | HPLC area % $T_5C^{Me}T_5$ | HPLC area % % $T_{11}$ | ratio HPLC area % $T_{11}/T_5C^{Me}T_5$ |
|---|---|---|---|
| 1 | 82,4 | 5,20 | 0,0630 |
| 2 | 83,3 | 5,11 | 0,00614 |
| 3 | 80,2 | 5,52 | 0,0688 |
| 4 | 80,5 | 5,92 | 0,0735 |
| Mean value | 81,6 | 5,44 | 0,0667 |

Figure 14:
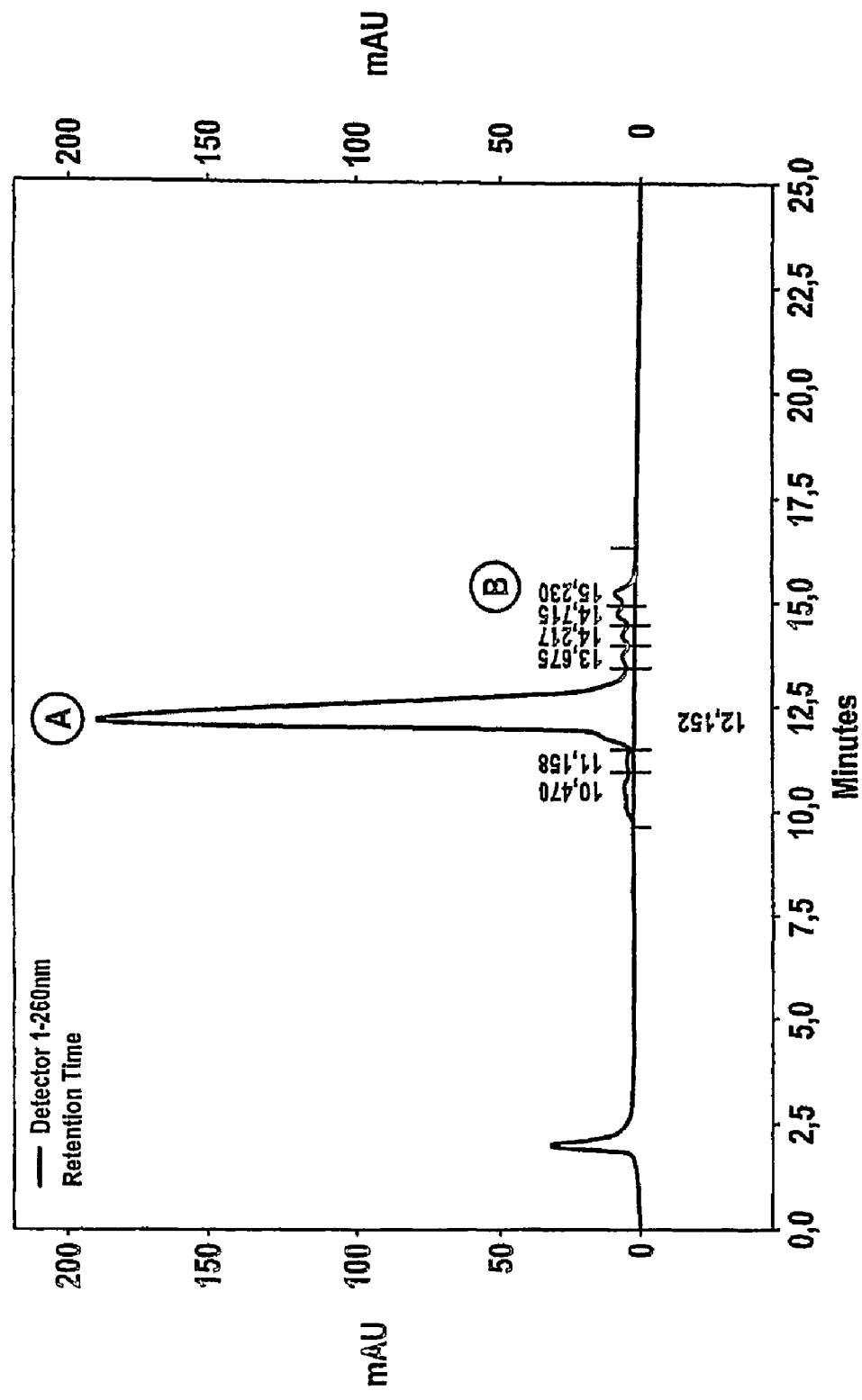

5 M bisulfite pH 5.5/T=80° C./t=2 h (optimized conditions) (see FIG. 14 for an exemplary chromatogram)

| sample | HPLC area % $T_5C^{Me}T_5$ | HPLC area % % $T_{11}$ | ratio HPLC area % $T_{11}/T_5C^{Me}T_5$ |
|---|---|---|---|
| 1 | 89,9 | 2,65 | 0,0295 |
| 2 | 89,5 | 2,46 | 0,0275 |
| 3 | 90,2 | 2,24 | 0,0248 |
| 4 | 89,7 | 2,88 | 0,0322 |
| Mean value | 89,8 | 2,56 | 0,0285 |

1.1.3 Conclusions

Conditions according to the invention lead to a similar product yield after 2 h reaction time as standard conditions after 8-16 h. Specificity of bisulfite reaction is significantly better for conditions according to the invention after 2 h compared to "standard conditions" after 16 h.

1.2 Comparison of Certain Conditions of the Bisulfite Method Using PCR of Bisulfite Treated Genomic DNA 1.2.1 General The fact that the bisulfite reaction has worked and converted non-methylated cytosines to uracil can also be demonstrated by a polymerase chain reaction whereby primers are used which are specific to a region of the nucleic acid sequence wherein non-methylated cytosines have been converted to uracils, i.e. the base adenine in the primer is opposite to the uracil being the bisulfite reaction product from non-methylated cytosines. In case of incomplete conversion, the primer could not hybridize to this region as there would be cytosines not matching the adenine bases in the primer. This would have the effect that no PCR product would be obtained.

An improved method to perform rapid polymerase chain reactions is disclosed e.g. in U.S. Pat. No. 6,174,670 and is used in the LightCycler® instrument (Roche, Mannheim, Germany). In this method, two labeled probes can come into close proximity in an amplificate dependent manner so that the two labels can perform a fluorescence energy transfer (FRET). The amount of the amplificate thereby correlates with the intensity of the emitted light of a certain wavelength. This specific PCR method can therefore be used to analyze whether a complete conversion of non-methylated cytosines was obtained, by e.g. analyzing the promoter region of the glutathion-S-transferase π gene (see e.g. U.S. Pat. No. 5,552,277, Genbank accession code M24485 and Morrow et al. (1989) Gene 75, 3-11) using suitable probes and primers. However, the expert skilled in the art knows that other methods can be used for this evaluation as well. Fluorescence measurements are normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement is the same for all reactions compared, so that all measurements represent increases relative to the same reaction cycle. In the early cycles of a polymerase chain reaction amplification, the number of target molecules can be described by the geometric equation $N_i=N_o \times (1+E)^i$, where $N_o$=the number of target molecules at the start of the reaction, $N_i$=the number of target molecules at the completion of the i-th cycle, E=the efficiency of the amplification ($0 \leq E \leq 1$). During this geometric growth phase of the amplification, the number of cycles required to reach a particular threshold value ($C_T$ value or crossing point) is inversely proportional to the logarithm of (1+E). Thus, the $C_T$ value represents a measure of the reaction efficiency that allows comparisons between reactions. A decrease in the $C_T$ value, which means that the reaction reached the threshold value in fewer cycles, indicates an increase in reaction efficiency. As the increase in amplification product is monitored by measuring the increase in reaction fluorescence, the $C_T$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau. An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value or crossing point, was calculated by interpolating fluorescence measurements between cycles.

1.2.2 Methods 1.2.2.1 Denaturation of DNA

100 μl of methylated DNA (Intergen, distributed by Serologicals Corporation, Norcross, Ga., USA; Cat S 7821) dilution (100 ng/assay spiked in 1000 ng human DNA background, Roche Cat.1691112; 4 replicates per method), and 12 μl 2 M NaOH are mixed and incubated for 15 min at 37° C.

1.2.2.2 Deamination of DNA

112 μl of the denatured DNA are mixed with 200 μl bisulfite reagent (2.5M sodium disulfite, 125 mM hydroquinone, pH 5.1) and incubated for 20 h at 50° C. ("Standard method")

or

112 μl of the denatured DNA are mixed with 200 μl bisulfite reagent (2.5M sodium disulfite, 125 mM hydroquinone, pH 5.5) and incubated for 2 h at 80° C. ("BIS-METHOD").

1.2.2.3 Processing Using Magnetic Glass Particles (MGPs)

312 μl of the deaminated DNA (from both methods respectively) are mixed with 600 μl binding buffer (MagNAPure DNA Isolation Kit I, Roche Cat. Nr. 3 003 990) and 75 μl magnetic glass particle solution (MagNAPure DNA Isolation Kit I) and incubated for 15 min/room temperature with continuous mixing in order to bind the nucleic acid to the MGPS according to the method described in the European patent applications with the numbers EP02019097.1 or EP02028114.3. Thereafter, the magnetic glass particles (MGPs) are washed three times with 1 ml 70% ethanol. Bound free separation is done in a magnetic separator (Roche Cat.1641794). Thereafter, desulfonation takes place by adding 250 μl 38% EtOH/100 mM NaCl/200 mM NaOH to the DNA bound to the MGPs; the mixture is incubated for 5 min at room temperature with mixing. Thereafter the MGPs are washed two times with 90% Ethanol. To get rid of ethanol rests the MGPs were heated for 15 min./60° C. in a thermomixer with open lid. Thereafter the DNA is eluted with 50 μl 10 mM Tris/0.1 mM EDTA pH 7.5 (15 min./60° C.). 10 μl of the eluted DNA is used for subsequent PCR analysis.

1.2.2.4 Detection of the Bisulfite Treated DNA by Using a Specific PCR on the LightCycler® Instrument (Hyprobe-Format)

1.2.2.4.1 Composition of Mastermix

LightCycler® FastStart DNA Master HybridizationProbe 1× (Roche 2239272), 2 mM MgCl$_2$, forward Primer 0.5 μM, reversed Primer 0.5 μM, donor probe 250 nM, acceptor probe 250 nM, template 10 μl, total PCR volume 20 μl.

1.2.2.4.2 PCR-Conditions
Denaturation 10 min/95° C.
55 cycles
- 95° C./10 s
- 65° C./10 s—signal acquisition
- 72° C./10 s Ramp time 20° C./s Samples were run in parallel in the same run on the Light-Cycler® instrument.

1.2.2.5 Results:

| Sample-Nr.* | BIS-Method | Ct-value | Median Ct-value |
|---|---|---|---|
| 1 | "standard" | 30.08 | |
| 2 | "standard" | 30.07 | |
| 3 | "standard" | 30.13 | |
| 4 | "standard" | 30.13 | 30.10 |
| 5 | "BIS Method" | 29.11 | |
| 6 | "BIS Method" | 30.14 | |
| 7 | "BIS Method" | 30.14 | |
| 8 | "BIS Method" | 29.58 | 29.74 |

The crossing points show that the "BIS Method" according to the invention is slightly more sensitive as the "standard" method.

1.2.3 Example: Variation of Temperature and Time of the Bisulfite Method According to the Invention The following experiments were performed using the experimental setup of the example under 1.2.1 whereby the temperature and the incubation time were varied and the indicated ct-values measured.

| Sample | Incubation time [min] | Ct-value | Temperature | Median Ct-value |
|---|---|---|---|---|
| 1 | 180 | 28.56 | 80° C. | 28.35 |
| 2 | 180 | 28.15 | 80° C. | |
| 3 | 180 | 28.03 | 80° C. | |
| 4 | 180 | 28.64 | 80° C. | |
| 5 | 150 | 28.86 | 80° C. | 28.57 |
| 6 | 150 | 28.64 | 80° C. | |
| 7 | 150 | 28.08 | 80° C. | |
| 8 | 150 | 28.71 | 80° C. | |
| 9 | 120 | 28.94 | 80° C. | 28.94 |
| 10 | 120 | 29.02 | 80° C. | |
| 11 | 120 | 28.77 | 80° C. | |
| 12 | 120 | 29.04 | 80° C. | |
| 13 | 90 | 29.76 | 80° C. | 29.67 |
| 14 | 90 | 29.76 | 80° C. | |
| 15 | 90 | 29.60 | 80° C. | |
| 16 | 90 | 29.57 | 80° C. | |
| 17 | 60 | 30.02 | 95° C. | 30.86 |
| 18 | 60 | 29.86 | 95° C. | |
| 19 | 60 | 33.54 | 95° C. | |
| 20 | 60 | 30.01 | 95° C. | |

This experiment shows that the extension of incubation time to 3 hours is not critical, whereas shortening of the incubation time to 90 min. results in a small loss of sensitivity. A higher loss of sensitivity resulted when the incubation time was shortened to 60 min but incubation temperature was elevated to 95° C.

LIST OF REFERENCES

Abramson, R. D., and Myers, T. W., Curr. Opin. Biotechnol. 4 (1993) 41-47
Ausubel, F., et al., in "Current protocols in molecular biology" (1994), eds. F. Ausubel, R. Brent and K. R. E., Wiley & Sons, New York
Barany, F., PCR Meth. Appl. 1 (1991) 5-16
Barany, F., Proc. Natl. Acad. Sci. USA 88 (1991) 189-193
Clark, S. J., et al., Nucl. Acids Res. 22 (1994) 2990-2997
EP 0 201 184
EP 0 389 063
EP 02 019 097
EP 02 028 114
EP-A 0 439 182
EP-A-0 200 362
Feil, R., et al., Nucl. Acids Res. 22 (1994) 695-696
Frommer, M., et al., Proc. Natl. Acad. Sci. USA 89 (1992) 1827-1831
Grigg, G., and Clark, S., Bioessays 16 (1994) 431-436
Grigg, G. W., DNA Seq. 6 (1996) 189-198
Grunau, C., et al., Nucl. Acids Res. 29 (2001) e65-5
Guatelli, J. C., et al., Proc. Natl. Acad. Sci. USA 87 (1990) 1874-1878
Hayatsu, H., et al., Biochem. 9 (1970) 2858-2865
Hayatsu, H., et al., J. Am. Chem. Soc. 92 (1970) 724-726
Komiyama, M., and Oshima, S., Tetrahedron Lett. 35 (1994) 8185-8188
Kwoh, D. Y., et al., Proc. Natl. Acad. Sci. USA 86 (1989) 1173-1177
Lottspeich and Zorbas, in "Bioanalytik" (1998), eds. L. a. Zorbas, Spektrum Akademischer Verlag, Heidelberg, Berlin, Germany
Oakeley, E. J., Pharmacol. Ther. 84 (1999) 389-400
Olek, A., et al., Nucl. Acids Res. 24 (1996) 5064-5066
Paulin, R., et al., Nucl. Acids Res. 26 (1998) 5009-5010
Raizis, A. M., et al., Anal. Biochem. 226 (1995) 161-166
Sambrook, J., et al., in "Molecular Cloning: A Laboratory Manual" (1989), eds. J. Sambrook, E. F. Fritsch and T. Maniatis, Cold Spring Harbor Laboratory Press, Cold Spring Harbor, N.Y.
Shapiro et al., JACS 92 (1970) 422-424
Slae and Shapiro, J. Org. Chem. 43 (1978) 4197-4200
Tasheva, E. S., and Roufa, D. J., Mol. Cell. Biol. 14 (1994) 5636-5644
U.S. Pat. No. 4,683,202
U.S. Pat. No. 5,130,238
U.S. Pat. No. 5,137,806
U.S. Pat. No. 5,210,015
U.S. Pat. No. 5,487,972
U.S. Pat. No. 5,595,890
U.S. Pat. No. 5,639,611
U.S. Pat. No. 5,786,146
U.S. Pat. No. 5,804,375
U.S. Pat. No. 6,174,670
U.S. Pat. No. 6,331,393
Wang, R. Y., et al., Nucl. Acids Res. 8 (1980) 4777-4790
Whelen, A. C., and Persing, D. H., Annu. Rev. Microbiol. 50 (1996) 349-373
WO 00/32762
WO 01/37291
WO 01/98528
WO 02/31186
WO 90/01069
WO 92/02638
WO 92/0880A
WO 96/41811
WO 99/16781
Wu, D. Y., and Wallace, R. B., Genomics 4 (1989) 560-569

What is claimed is:

1. Method for the conversion of a cytosine base in a nucleic acid to an uracil base comprising
   a) incubating a solution comprising the nucleic acid for a time period that is not less than 1.5 hours and further is not more than 3.5 hours at a temperature between 70 and 90° C., wherein the concentration of bisulfite in the solution is between 3 M and 6.25 M and wherein the pH value of the solution is between 5.25 and 5.75, whereby the nucleic acid is deaminated, and
   b) incubating the solution comprising the deaminated nucleic acid under alkaline conditions whereby the deaminated nucleic acid is desulfonated.

2. Method according to claim 1, wherein in step a) the temperature is between 75 and 85° C.

3. Method according to claim 1, wherein the concentration of bisulfite is between 3.2 M and 6 M.

4. Method according to claim 1, wherein the time period is between 1.75 and 3 hours.

5. Method according to claim 1, wherein the time period is between 2 and 3 hours.

6. Method according to claim 1, wherein in step a) the temperature is 80° C., the concentration of bisulfite is 5 M, the pH value of the solution is 5.5 and the time period is between 2 and 3 hours.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:sense strand

<400> SEQUENCE: 1
gaggggcgcc ctggagtccc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:antisense
      strand

<400> SEQUENCE: 2
gggactccag ggcgcccctc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:sense
      strand, c converted to n, n denotes deoxyuracil

<400> SEQUENCE: 3 gagggngnn ntggagtnnn                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:antisense
      strand, c converted to n, n denotes deoxyuracil

<400> SEQUENCE: 4
gggantnnag ggngnnnntn                                              20

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence:synthesized
      oligonucleotide

<400> SEQUENCE: 5
tttttctttt t                                                       11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:synthesized
      oligonucleotide, c in position 6 is methylated

<400> SEQUENCE: 6

```
tttttctttt t                                                     11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence:synthesized
      oligonucleotide, c converted to n, n denotes deoxyuracil

<400> SEQUENCE: 7
tttttntttt t                                                     11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence:synthesized
      oligonucleotide

<400> SEQUENCE: 8
tttttttttt t                                                     11
```